United States Patent [19]

Drobish et al.

[11] Patent Number: 4,623,329
[45] Date of Patent: Nov. 18, 1986

[54] DRAINAGE AND INFUSION CATHETERS HAVING A CAPILLARY SLEEVE FORMING A RESERVOIR FOR A FLUID ANTIMICROBIAL AGENT

[75] Inventors: James L. Drobish; Eldon G. Spletzer, both of Cincinnati; Hugh A. Thompson, Fairfield, all of Ohio

[73] Assignee: The Procter & Gamble Company, Cincinnati, Ohio

[21] Appl. No.: 561,840

[22] Filed: Dec. 15, 1983

[51] Int. Cl.[4] .............................................. A61M 25/00
[52] U.S. Cl. ...................................... 604/29; 604/265; 604/43
[58] Field of Search ...................... 604/29, 27, 43, 45, 604/265, 266, 280–284, 101, 103

[56] References Cited

U.S. PATENT DOCUMENTS

| | | | |
|---|---|---|---|
| 1,045,326 | 11/1912 | Ruffin | 604/43 |
| 3,394,705 | 7/1968 | Abramson | 128/349 |
| 3,583,404 | 6/1971 | McWhorter | 604/43 |
| 3,598,127 | 8/1971 | Wepsic | 604/265 |
| 3,699,956 | 10/1972 | Kitrilakis et al. | 128/348 |
| 3,753,439 | 8/1973 | Brugarolas | 604/43 |
| 3,854,480 | 12/1974 | Zaffaroni | 128/260 |
| 3,948,273 | 4/1976 | Sanders | 604/280 |
| 3,981,299 | 9/1976 | Murray | 128/349 |
| 4,186,745 | 2/1980 | Lewis et al. | 128/349 R |
| 4,198,984 | 4/1980 | Taylor | 604/280 |
| 4,214,593 | 7/1980 | Imbruce et al. | 604/45 |
| 4,483,688 | 11/1984 | Akiyama | 604/265 |

Primary Examiner—C. Fred Rosenbaum
Assistant Examiner—Karen L. Kaechele
Attorney, Agent, or Firm—Frost & Jacobs

[57] ABSTRACT

A catheter for drainage of or infusion into a body cavity. The catheter comprises an elongated tubular shaft having a distal end provided with at least one port near the distal end and intended to be located in the body cavity. The catheter has an open proximal end for connection to a drain, suction conduit or infusion line. A sleeve is mounted about the shaft extending along a portion at least of the internal body surface contacting part thereof between its proximal and distal ends. The sleeve forms a substantially concentric fluid reservoir between the drainage tube and the sleeve. Filling means are provided at the proximal end of the shaft for supplying to the reservoir a fluid antimicrobial agent capable of controlled passage through the sleeve by diffusion. The inner surface of the sleeve is provided with a plurality of longitudinally extending capillary channels or grooves providing uniform distribution of the fluid antimicrobial agent within the reservoir and throughout the length of the reservoir.

13 Claims, 6 Drawing Figures

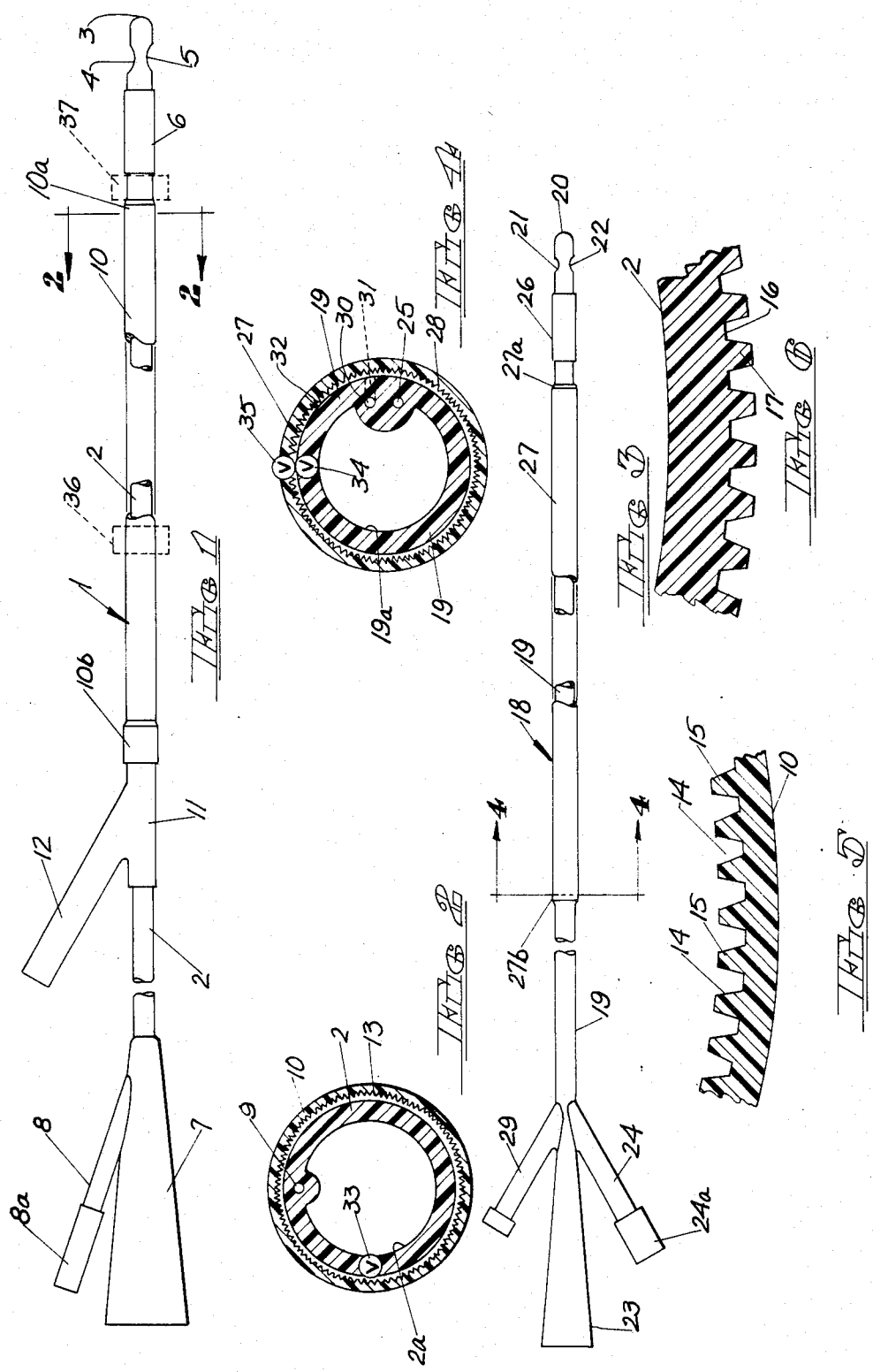

DRAINAGE AND INFUSION CATHETERS HAVING A CAPILLARY SLEEVE FORMING A RESERVOIR FOR A FLUID ANTIMICROBIAL AGENT

REFERENCE TO RELATED APPLICATION

The present application is related to commonly-owned co-pending application Ser. No. 06/561,738, filed concurrently herewith in the names of Mark M. Anderson, Donald S. Lucas and Robert V. Mustacich, and entitled "A METHOD OF DRAINAGE AND INFUSION CATHETERIZATION WITH LOWERED RISK OF CATHETER-INDUCED AND-ASSOCIATED INFECTIONS", said application being hereby incorporated herein by reference.

TECHNICAL FIELD

The invention relates to drainage and infusion catheters for human and animal use, and more particularly to such catheters having a sleeve forming a reservoir about the catheter for a fluid antimicrobial agent capable of passage through the sleeve by diffusion and means within the sleeve to assure uniform distribution of the fluid antimicrobial agent throughout the length of the sleeve.

BACKGROUND ART

Insertion of catheters into the human body for therapeutic purposes carries the risk of infection which can, under certain circumstances, be life-threatening. For example, in the case of a urine drainage catheter inserted into the bladder via the urethra, this risk increases with the duration of catheterization and may be compounded by the presence of antibiotic-resistant microorganisms which are often endemic in hospital environments. Although the incidence of infection varies among hospitals, up to 45% of catheterized patients may acquire a urinary tract infection by three days of continuous catheterization. Catheter-induced urinary tract infections presenting as bacteriuria may resolve spontaneously on removal of the catheter or may require aggressive treatment with antibiotics and prolonged hospitalization. Severe cases may result in urethral scarring, kidney damage, or bacteremia, with corresponding morbidity and mortality. It has been estimated that of the 7.5 million patients per year who require indwelling urinary catheterizations, approximately 500,000 will acquire a catheter-associated urinary tract infection.* This results in an average of two additional days of hospitalization per infection, resulting in additional direct health care costs in excess of $500 million per year. Nosocomial urinary tract infections have been cited as the underlying cause of up to 56,000 deaths per year in the United States.*

*Platt, R.; Polk, B. F.; Murdock, B.; Rosner, B.; "Mortality Associated With Nosocomial Urinary-Tract Infection", The New England Journal of Medicine, 303 (1982) 638–642.

Potentially, the sleeved antimicrobial catheter of the present invention could be beneficial in any case where tubing must be inserted in the body. Obviously, such catheters will be most valuable in situations where infection is most likely. Aside from urinary catheterization, these situations generally involve artificial body openings. Examples of catheterization to which the teachings of the present invention could be advantageously applied include peritoneal dialysis catheters, hyperalimentation catheters, catheters associated with insulin delivery pumps, surgical drains, embolectomy catheters, cardiovascular catheters and intravenous catheters. For purposes of an exemplary showing, the teachings of the present invention will be described in terms of their application to a urethral catheter. This is a matter of convenience, only, and no limitation should be inferred therefrom except as stated in the claims hereinafter.

Prior art workers have developed numerous types of urethral catheters having associated means for antiseptic treatment of the urethra. U.S. Pat. No. 3,394,705 issued July 30, 1968 in the name of D. J. Abramson is exemplary. This reference teaches a drainage balloon catheter comprising two concentric tubes, one within the other. The inner tube constitutes a drainage tube. The outer tube is provided with a plurality of openings uniformly spaced in a spiral thereabout. Suction may be periodically applied to the outer tube for removal of infected matter from the urethra. Similarly, an antiseptic fluid may be injected through the outer tubing to irrigate the urethra and prevent spread of infection. U.S. Pat. No. 3,598,127, issued Aug. 10, 1971 in the name of James G. Wepsic, teaches a catheter comprising a nonpermeable drainage tube having a multiplicity of grooves formed in its periphery. The grooves are filled with a medicament and are covered with a sheath permeable by the medicament. Thus, each groove in the catheter constitutes a sort of non-replenishable medicament reservoir.

U.S. Pat. No. 3,981,299, issued Sept. 21, 1976 in the name of H. E. Murray, discloses a urethal catheter in the form of a triple lumen catheter having a highly porous rubber outer membrane for delivery of medication to the urethra. The drainage tube within the highly porous membrane is provided with a plurality of projections to properly space the membrane from the drainage tube. The catheter of this patent, like that of the above mentioned U.S. Pat. No. 3,394,705, is an irrigation device which does not provide diffusion and controlled release of the medicament. Finally, U.S. Pat. No. 4,186,745, issued Feb. 5, 1980 in the name of D. W. Lewis, discloses still another porous catheter comprised of a micropore structure which can be charged with certain substances that will minimize infections normally associated with the use of catheters. In one embodiment, the catheter is provided with a multiplicity of longitudinally extending passages spaced circumferentially about the catheter body and interconnected to one another by a circumferential passage through which a medicament can be introduced into the passage system. The catheter is made of porous material which allows the fluid retained therein to be released.

The controlled delivery of a medicament over a long period of time by diffusion through a membrane is not, per se, new. For example, U.S. Pat. No. 3,854,480, issued Dec. 17, 1974 to A. Zaffaroni describes a drug delivery system comprising a solid inner matrix material having solid particles of drug dispersed therethrough, surrounded by an outer polymeric membrane, insoluble to body fluids. Both the inner matrix material and the outer polymeric membrane are permeable to passage of the drug by diffusion, with the drug diffusing through the polymeric membrane at a lesser rate than through the solid inner matrix. However, such a structure would not be practical for catheters of the type contemplated herein.

In a urinary catheter wherein the reservoir is charged with an antimicrobial solution, the fluid antimicrobial agent preferably should be released along the entire length of the urethra from the meatus inward. This allows for attack of microbes already in the urethra at the time of catheterization as well as organisms that attempt to migrate into the space between the urethra and the catheter. The same principle is generally true in the use of non-urinary catheters. Ideally, the entire length that is inserted into the body should be capable of of delivering the fluid antimicrobial agent. In instances where a fluid antimicrobial agent is used to which internal tissues are less sensitive than external epithelial tissues, the sleeve should be of such length that it does not extend outside the body, or if it does, that portion of the sleeve extending outside the body can be coated with a material impervious to the fluid antimicrobial agent. Furthermore, the release of the fluid antimicrobial agent should not exceed that required for microbiocidal effacacy, since a greater release would have no beneficial effect.

Prior art catheters intended to dispense a fluid antimicrobial agent or other fluid material are frequently characterized by insufficient or uncontrolled release of the fluid material. Another problem lies in the fact that delivery of the fluid material is frequently asymmetric and non-uniform about the catheter or non-uniform throughout the length of that much of the catheter in contact with the body. Often, antimicrobial action of the catheter is of limited duration and without provision for replenishment.

The catheter structure of the present invention provides a concentric, replenishable fluid antimicrobial agent reservoir about the shaft or drainage tube of the catheter. The antimicrobial agent in the fluid material is dispensed by diffusion through the sleeve. The release rate of the fluid antimicrobial agent can be varied conveniently by adjusting the concentration of the fluid antimicrobial agent and the composition and thickness of the sleeve. The provision of longitudinally extending capillary grooves upon the inside surface of the sleeve will assure uniform distribution of the fluid antimicrobial agent throughout the length of the sleeve; will hold the fluid antimicrobial agent at the surface of the sleeve; will assure availablity of the fluid antimicrobial agent to areas where the sleeve is held intimately against the drainage tube of the catheter; and will help prevent adhesion of the sleeve to the drainage tube of the catheter.

DISCLOSURE OF THE INVENTION

According to the invention there is provided a catheter for the drainage and/or introduction of fluids into a body cavity. The catheter comprises an elongated shaft in the form of a drainage tube or an infusion tube. The shaft has a distal end provided with at least one port and intended to be located in the body cavity to be drained or infused. The opposite or proximal end of the shaft is open and intended for connection to a drain, suction conduit or infusion conduit. In this case, "distal" refers to the end of the catheter inserted into the patient. "Proximal" refers to the end furthest from the patient. The drainage shaft may be provided with a retention balloon near its distal end, as is well known in the art.

A sleeve is mounted about the shaft and extends along the portion thereof in contact with internal body surfaces from a position near the retaining balloon (if present) toward the proximal end of the shaft. The length of the sleeve, of course, can be varied depending upon the particular use for which the catheter is intended. The sleeve is sealed at its ends to the shaft and forms a substantially concentric fluid reservoir between the shaft and the sleeve.

Filling means are provided at the proximal end of the shaft for supplying to the reservoir a fluid antimicrobial agent capable of controlled passage through the sleeve by diffusion. The filling means comprises a branch on the shaft capable of accepting the fluid antimicrobial agent by means of a hypodermic needle, a syringe, or other appropriate means. The branch may be connected directly to the proximal end of the sleeve. Alternatively, the inlet branch may be connected to a lumen in the wall of the shaft, which lumen opens into the reservoir at its proximal end or its distal end.

The reservoir may be provided with a valved drain port through which spent fluid antimicrobial agent and/or air may be vented upon the introduction of fresh fluid antimicrobial agent. The valved drain port may be formed in the drainage or infusion tube wall so as to discharge the spent fluid antimicrobial agent or air into the drainage or infusion tube. The valved drain port should be located at that end of the reservoir opposite the end from which the reservoir is filled. If the reservoir is filled from its distal end, the valved drain port could be located in the sleeve, itself, adjacent its proximal end. Under these circumstances, the valved drain port in the sleeve could be connected to a collection device. The presence of a valved drain port also permits continuous pumping of fresh fluid antimicrobial agent through the reservoir.

The inner surface of the sleeve is provided with a plurality of longitudinally extending capillary grooves which provide uniform distribution of the fluid material within the reservoir and throughout the length thereof by capillary action. The grooves serve additionally to hold the fluid material at the surface of the sleeve by capillary action. To ensure that capillary action is provided by the grooves, the material in which the grooves are provided preferably exhibits a favorable surface contact angle for the particular fluid antimicrobial agent to be dispensed, i.e., its surface is chosen to be either hydrophilic for fluid antimicrobial agents containing primarily water or oleophilic for fluid antimicrobial agents containing primarily oil.

In addition to the benefits provided by capillary action, the grooves serve to prevent adhesion of the sleeve to the shaft of the catheter. Uniform distribution of the fluid material occurs even when portions of the sleeve are held intimately against the shaft of the catheter. The capillary grooves could be located on the exterior surface of the shaft, rather than the inner surface of the sleeve, as will be described hereinafter.

BRIEF DESCRIPTION OF THE DRAWINGS

FIG. 1 is a fragmentary elevational view of a catheter according to the present invention.

FIG. 2 is a cross sectional view taken along section line 2—2 of FIG. 1.

FIG. 3 is a fragmentary elevational view of the second embodiment of the catheter of the present invention.

FIG. 4 is a cross sectional view taken along section line 4—4 of FIG. 3.

FIG. 5 is an enlarged, fragmentary, cross sectional view of the sleeve of the present invention.

FIG. 6 is an enlarged, fragmentary, cross sectional view of the shaft or drainage tube portion covered by the sleeve.

DETAILED DESCRIPTION OF THE INVENTION

A first embodiment of the present invention (in the form of a urethral drainage catheter) is illustrated in FIGS. 1 and 2, wherein like parts have been given like index numerals. The catheter is generally indicated at 1 and comprises a shaft or drainage tube 2 having a closed and rounded distal end 3. Near its distal end, the drainage tube 2 may be provided with one or more inlet ports. Two such inlet ports, in diametrically opposed position, are shown at 4 and 5. The distal end 3 of drainage tube 2 (including the inlet ports 4 and 5) is intended to be located within the body cavity to be drained. Since, for purposes of an exemplary showing the catheter 1 is illustrated as a urethral drainage catheter, the body cavity to be drained would be the patient's bladder. To assure proper retention of the distal end 3 of the catheter within the cavity to be drained, the catheter may be provided with an expandable balloon 6, as is well known in the art.

At its proximal end, the drainage tube 2 is provided with a fitting 7 enabling the drainage tube to be connected to an appropriate and conventional drainage conduit, suction line or the like. Additionally, a conventional fluid port 8 is provided. The fluid port 8 is connected to a lumen 9 (see FIG. 2) formed in the wall of drainage tube 2 and leading to the retention balloon 6. By means of fluid port 8 and lumen 9, the balloon 6 can be inflated through the introduction of an appropriate fluid material. Fluid port 8 may be provided with a one-way filling valve 8a, as is well known in the art. Drainage tube 2, fitting 7, and fluid port 8 may constitute a one-piece, integral structure molded of any rubber or plastic material which is soft and flexible, suitable for use in a surgical environment and in contact with the body, compatible with the fluid antimicrobial agent used, and capable of being sterilized by any one or more of the well known methods.

Mounted on the exterior of the drainage tube 2 there is a sheath or sleeve 10. The distal end 10a of sleeve 10 is located near balloon 6 and is sealed by any appropriate means to the exterior of drainage tube 2. The sleeve 10 should be of such length as to cover at least a portion of that part of drainage tube 2 which would normally be in contact with internal surfaces of the body. A fitting 11, providing a filling port 12, is mounted on drainage tube 2 near its proximal end and is sealed thereto. The proximal end 10b of sleeve 10 engages the forward portion of fitting 11 and is sealed thereto. As a result, sleeve 10, in conjunction with the coextensive portion of drainage tube 2, forms a reservoir 13 (see FIG. 2). A fluid antimicrobial agent can be introduced into reservoir 13 via filling port 12, through the use of a hypodermic needle or the like. The nature of port 12 does not constitute a limitation on the present invention. The reservoir 13 could be filled by a syringe or any other appropriate means.

The fitting 11 is preferably made of a flexible plastic material suitable for a surgical environment and capable of being sterilized. The fitting 11, could, indeed, constitute an integral part of the drainage tube, connected to the proximal end of reservoir 13 by a lumen (not shown) similar to lumen 9 of FIG. 2.

The reservoir 13 is intended to be filled with a fluid antimicrobial agent. The sleeve 10 is permeable to the passage of the agent by diffusion at a controlled release rate sufficient to reach an effective antimicrobial concentration at the aqueous catheter-urethra interface. The material from which sleeve 10 is made is chosen to be soft and pliable, capable of appropriate fabrication, safe for use in a surgical environment and in contact with the body, capable of being sterilized by at least one of the well known sterilization procedures and appropriately permeable to the passage of the fluid antimicrobial agent within reservoir 13. The material for the shaft or drainage tube 2 has the same requirements except that it may or may not need to be permeable to the fluid antimicrobial agent, depending upon the intended use of the catheter, as will be described hereinafter. To ensure that the grooves provided in the sleeve or shaft provide uniform distribution of the fluid antimicrobial agent along the length of the sleeve and also that the grooves preferentially hold the material at the base of the grooves by capillary action, the material in which the grooves are provided preferably exhibits a favorable surface contact angle for the particular fluid antimicrobial agent to be dispensed, i.e., its surface is chosen to be hydrophilic for fluid antimicrobial agents containing primarily water or oleophilic for fluid antimicrobial agents containing primarily oil. It is, of course, recognized that surface treatments well known in the art can be utilized to alter the surface contact angle of the materials of construction in the event the materials of construction do not inherently exhibit the desired surface contact angle. Non-limiting examples of materials from which the sleeve 10 and the shaft 2 can be made include silicone polymers and copolymers, polyurethanes, ethylene vinyl acetate copolymers and butadiene-styrene copolymers.

FIG. 5 is an enlarged fragmentary cross sectional view of the sleeve 10. It will be noted that the inside surface of sleeve 10 has a plurality of longitudinal capillary channels or grooves 14 formed therein. The grooves 14 extend the length of the sleeve 10 in parallel spaced relationship. The grooves 14 serve a number of purposes. Primary among these is the fact that, acting as capillary channels, they assure that the fluid antimicrobial agent within the reservoir extends the entire length of the reservoir by capillary action. Similarly, the capillary action of the grooves 14 tends to retain the fluid material introduced into the reservoir adjacent the vertices of the grooves and thus holds the fluid material at the surface of the sleeve 10. As a result, the capillary grooves provide uniform distribution of the fluid material inside the sleeve 10 and assure availability of the fluid material to areas where the sleeve is held intimately against the shaft or drainage tube 2. Thus, the sleeve portions 15 between the grooves 14 also serve as spacers for sleeve 10 with respect to drainage tube 2. All of this provides for a uniform volume of fluid antimicrobial agent at each dosing. Further, this structure of sleeve 10 helps to prevent adhesion of the sleeve to the exterior surface of drainage tube 2 by minimizing the area of contact.

A particularly preferred method of drainage and infusion catheterization with lowered risk of catheter-induced and -associated infections using catheters of the present invention is disclosed in the commonly-owned co-pending application Ser. No. 06/561,738, filed concurrently herewith in the names of Mark. M. Anderson, Donald S. Lucas and Robert V. Mustacich, and entitled "A METHOD OF DRAINAGE AND INFUSION CATHETERIZATION WITH LOWERED RISK OF CATHETER-INDUCED AND -ASSOCIATED INFECTIONS", said application being incorporated herein by reference. For fluid antimicrobial solutions of the type disclosed in the aforementioned patent application of Anderson, et al., i.e., those containing a straight-chain carboxylic acid having from 6 to 12 carbon atoms (and mixtures of such acids) at a concentration sufficient to maintain a minimum lethal release rate thereof through the sleeve cidal to pathogenic microorganisms at the placement site of the catheter, the sleeve 10 on a catheter of the present invention is contemplated as having a thickness of from about 0.003 to about 0.030 inches. While both the dimensions and the geometry of the capillary grooves 14 can be varied, excellent results have been achieved using such fluid antimicrobial solutions with grooves having tapered walls and a depth dimension of from about 0.001 to about 0.010 inch. The depth of the grooves should be in the range of 0.5 to 5 times their nominal width, depending upon the overall thickness of the sleeve 10. The grooves are placed symmetrically around the inner circumference of sleeve 10.

It is also within the scope of the invention to provide similar grooves in the exterior surface of drainage tube 2, in lieu of the grooves 14 in sleeve 10. Provided the grooves are sized to prevent intermeshing engagement with one another at the points of contact, grooves can, if desired, be provided in both surfaces. Alternatively, if the grooves are similarly sized, it may still be possible to prevent intermeshing engagement of the opposing surfaces by orienting the grooves in the sleeve in a spiral wound arrangement (oriented, for example, in a clockwise direction) and orienting the grooves in the shaft in a spiral wound arrangement (oriented in a counter-clockwise direction). FIG. 6 is an enlarged fragmentary cross sectional view of drainage tube 2. Formed in its surface is a plurality of capillary grooves 16 with intermediate portions 17 therebetween. The capillary grooves extend longitudinally of drainage tube 2. The capillary grooves 16 serve substantially the same purpose as capillary grooves 14, helping to prevent adhesion of sleeve 10 and drainage tube 2 while assuring availability of the fluid antimicrobial agent throughout the length of reservoir 13.

It is also within the scope of the present invention to make the shaft or drainage tube 2, or at least that portion thereof covered by sleeve 10, permeable to the passage of the fluid antimicrobial agent by diffusion. This would provide antibacterial activity to the urine-carrying lumen 2a of drainage tube 2 and to the collection means (not shown) to which it is attached, both constituting sources of infection in the bladder.

FIG. 3 illustrates a second embodiment of the catheter of the present invention. The catheter is generally indicated at 18 and comprises a shaft or drainage tube 19. The drainage tube 19 has a closed distal end 20 provided with drainage inlet ports 21 and 22, similar to inlet ports 4 and 5 of FIG. 1. At its proximal end, the drainage tube 19 terminates in an integral fitting 23 by which it may be attached to a drainage or suction conduit in the conventional manner. Near its proximal end, a fluid inlet port 24 is provided, having a one-way filling valve 24a. The inlet port 24 is connected by a lumen 25 formed in the wall of drainage tube 19 and leading to a retention balloon 26. The retention balloon 26 is similar to balloon 6, described with respect to FIG. 1.

The catheter 18 is provided with a sleeve 27, similar to sleeve 10 of FIG. 1. The sleeve 27 extends from a position adjacent balloon 26 toward the proximal end of the catheter, and again should be of such length as to cover at least a portion of that part of catheter 18 in contact with the internal body surfaces. The sleeve 27 has a distal end 27a and a proximal end 27b, both of which are sealed to the drainage tube 19. In this way, the sleeve 27 and drainage tube 19 define a reservoir 28 (see FIG. 4). The reservoir 28 is intended to serve the same purpose as reservoir 13 of FIG. 2. Thus, reservoir 28 is adapted to contain a fluid antimicrobial agent. Sleeve 27 is permeable to the controlled pasage of the fluid antimicrobial agent therethrough by diffusion.

The catheter 18 is provided with an inlet port 29. The inlet port constitutes an integral one-piece part of the shaft or drainage tube 19 and may be configured to accept a syringe, a hypodermic needle or the like. The inlet port 29 is connected to a second lumen 30 formed in the wall of drainage tube 19 (see FIG. 4). The lumen 30 terminates in a lateral passage 31 opening through the exterior surface of the wall of drainage tube 19 to reservoir 28. While the lateral passage 31 could be located at the proximal end of reservoir 28, it is preferred that it be located near the distal end of reservoir 28, as defined by the sealed distal end 27a of sleeve 27. By means of inlet port 29, lumen 30 and lateral passage 31, the fluid antimicrobial agent can be introduced into reservoir 28.

The inside surface of sleeve 27 is provided with a plurality of capillary grooves 32, equivalent to the capillary grooves 14 of sleeve 10. Thus, for purposes of this description, FIG. 5 could also be considered to be an enlarged, fragmentary, cross sectional view of sleeve 27. The grooves 32 extend longitudinally of the sleeve and serve the very same purposes described with respect to capillary grooves 14 of sleeve 10.

It is also within the scope of the present invention to provide capillary grooves on the exterior surface of drainage tube 19 in lieu of the grooves 32, similar to capillary grooves 16 illustrated in FIG. 6. Thus, FIG. 6 could also be considered to be an enlarged, fragmentary, cross-sectional view of drainage tube 19. Such capillary grooves formed in the exterior surface of drainage tube 19 extend longitudinally thereof at least in that portion of its exterior peripheral surface which defines reservoir 28. Such grooves would serve the same purposes described with respect to the capillary grooves 16 of FIG. 6. Furthermore, it would be within the scope of the present invention to make drainage tube 19 (or at least that portion defining reservoir 28) permeable to the fluid antimicrobial agent so as to provide antibacterial activity directly to the urine-carrying lumen 19a of drainage tube 19 and the collection means (not shown) to which it is connected.

It is within the scope of the present invention to provide both embodiments of the catheter of the present invention with a valved outlet port for the reservoir. The valved outlet port of the reservoir should be located at that end of the reservoir opposite the end from which the reservoir is filled.

Turning first to the embodiment of FIGS. 1 and 2, the sleeve 10, forming reservoir 13, is filled from its proximal end by means of fitting 11 and filling port 12. A valved outlet port, indicated at 33 in FIG. 2, can be located in the wall of drainage tube 2. The valved outlet port 33 connects reservoir 13 with the main drainage lumen 2a of drainage tube 2 and is of such nature that fluid material can pass therethrough only from the reservoir 13 to the lumen 2a, and not vice versa. The valved port 33 should be located at the distal end of reservoir 13.

In the catheter embodiment illustrated in FIGS. 3 and 4, the reservoir 28 is filled by means of inlet port 29, lumen 30 and lateral passage 31. As indicated above, lateral passage 31 could be located at the proximal end of reservoir 28, but is preferably located at the distal end thereof. In this embodiment, the wall of drainage tube 19 may be provided with a one-way valved outlet port, shown at 34 in FIG. 4. The valved outlet port 34 is substantially identical to valved outlet port 33 of FIG. 2. When the lateral passage 31 is located at the proximal end of reservoir 28, the valved outlet port 34 should be located at the distal end thereof. When lateral passage 31 is located at the distal end of reservoir 28, then the valved outlet port 34 should be located at or near the proximal end thereof.

When the lateral passage 31 is located at the distal end of reservoir 28, it would be within the scope of the present invention to provide a valved outlet port at the proximal end of the reservoir in the sleeve 27, rather than in the wall of drainage tube 19. Such a valved outlet port is illustrated at 35 in FIG. 4 and is so arranged as to allow flow of fluid from the reservoir through the port, only. The valved outlet port 35 would be located outside the body and could be connected to a collection means (not shown).

Valved outlet ports, such as those shown at 33 in FIG. 2 and 34 or 35 in FIG. 4, have several purposes. First of all, when the reservoir 13 or 28 is charged with a fluid antimicrobial agent, it will be apparent that the reservoir is full and free of air when the solution begins to run through the valved outlet port. Similarly, when the reservoir 13 or 28 is recharged with a fluid antimicrobial agent, spent diluent and trapped air can more easily be vented by means of valved outlet port 33, 34 or 35. Furthermore, the presence of a valved port, such as those just described, would enable a continuous flow of fluid antimicrobial agent to be pumped through reservoir 13 or 28 which, in some instances, is advantageous. When the valved port is located in the wall of the drainage tube 2 (such as valved port 33) or drainage tube 19 (such as valved port 34), this would permit antimicrobial treatment of the urine-carrying lumen 2a or 19a and its collection means (not shown) to help prevent microbial movement through the lumen to the patient's bladder.

The catheters of FIGS. 1 and 3 each provide a concentric, replenishable drug reservoir for fluid antimicrobial agents. They are characterized by symmetrical, sustained release of the fluid antimicrobial agent. Since the reservoir of each is rechargable, the fluid antimicrobial agent may be delivered repeatedly, giving the antimicrobial properties of the catheter an indefinite life. The fact that the release of the fluid antimicrobial agent is symmetrical gives complete and uniform radial protection to the urethra. Uniform longitudinal protection is assured by the capillary grooves of the sleeve or the drainage tube, within the reservoir.

As indicated above, the embodiments just described are both urethral catheters, i.e. of the drainage type. The catheters of FIGS. 1 and 3 could readily be modified to be infusion catheters. For example, in an infusion catheter, the fittings 7 (FIG. 1) and 23 (FIG. 3) would be conventional fittings enabling the catheters to be connected to an appropriate source of infusate. Shafts 2 and 19 would constitute infusion tubes and would be provided an appropriate arrangement of outlet ports (similar to ports 4, 5 and 21, 22) at their distal ends. Depending upon the application of the catheters, the retention balloons 6 and 26, the lumens 9 and 25 and the fluid ports 8 and 24 could be eliminated. In all other respects, the infusion catheters would be substantially the same as the embodiments of FIGS. 1 and 3, differing, of course, in length, diameter and the like, depending upon their application.

In the case of a continuous ambulatory peritoneal dialysis (CAPD) catheter, the device serves as both an infusion and a drainage catheter. The embodiments of FIGS. 1 and 3 can readily be modified to constitute a CAPD catheter. In the embodiment of FIG. 1, the retention balloon, lumen 9 and fluid port 8 would be eliminated. The fitting 7 at the proximal end of shaft 2 would be designed to mate with an appropriate connector at the end of a tube leading to a bag of dialysis fluid. The distal portion of the shaft will be provided with an appropriate arrangement of ports, similar to ports 4 and 5, and serving as both inlet and outlet ports. The catheter 1 would be provided with a pair of spaced conventional anchoring cuffs, the proximal one of which is surgically placed just under the skin of the patient and the distal one of which is located deeper in the muscle of the abdominal wall. The proximal anchoring cuff is shown in broken lines at 36 in FIG. 1 and the distal anchoring cuff is shown in broken lines at 37. The sleeve 10 would extend from the distal anchoring cuff 37, beneath the proximal anchoring cuff 36, to a position outside the patient's body. In all other respects, the catheter of FIG. 1 would be substantially the same as described above with the exception that the distal portion of the catheter beyond anchoring cuff 37 would be longer. It will be understood by one skilled in the art that the embodiment of FIG. 3 could be similarly modified to form a CAPD catheter.

Modifications may be made in the invention without departing from the spirit of it.

What is claimed is:

1. A catheter for drainage of or infusion into a body cavity, said catheter comprising an elongated tubular shaft having a distal end with at least one port near said distal end to be located in said body cavity to be treated and an open proximal end adapted to be connected to a drainage or infusion conduit, a sleeve extending about and longitudinally of said shaft from a point near said at least one port toward said proximal end of said shaft, said sleeve forming a concentric reservoir for a fluid antimicrobial agent, said sleeve being permeable to the controlled passage of said fluid antimicrobial agent by diffusion, filling means at said proximal end of said shaft for supplying said fluid antimicrobial agent to said reservoir and for replenishing said fluid antimicrobial agent therein, said sleeve having a distal end sealed to said shaft, said sleeve having a proximal end sealed to one of said shaft and said filling means, and distribution means for distributing said fluid antimicrobial agent within said reservoir about the periphery of said reservoir and for transporting said fluid antimicrobial agent along the length of said reservoir, said distribution means comprising a plurality of capillary grooves formed in the inside surface of said sleeve, said grooves being in parallel side-by-side relationship and extending the length of said sleeve.

2. The catheter of claim 1, wherein said sleeve containing said grooves exhibits a surface contact angle with respect to said fluid antimicrobial agent which will promote distribution of said fluid antimicrobial agent along the length of said sleeve and preferentially hold said fluid antimicrobial agent at the base of said grooves by capillary action.

3. The catheter claimed in claim 1, wherein said capillary grooves formed in said inside surface of said sleeve have a nominal width in the range of from about 0.001 to about 0.010 inch and a depth of from about 0.5 to about 5 times the nominal width.

4. A catheter for drainage of or infusion into a body cavity, said catheter comprising an elongated tubular shaft having a distal end with at least one port near said distal end to be located in said body cavity to be treated and an open proximal end adapted to be connected to a drainage or infusion conduit, a sleeve extending about and longitudinally of said shaft from a point near said at least one port toward said proximal end of said shaft, said sleeve forming a concentric reservoir for a fluid antimicrobial agent, said sleeve being permeable to the controlled passage of said fluid antimicrobial agent by diffusion, filling means at said proximal end of said shaft for supplying said fluid antimicrobial agent to said reservoir and for replenishing said fluid antimicrobial agent therein, said sleeve having a distal end sealed to said shaft, said sleeve having a proximal end sealed to one of said shaft and said filling means, and distribution means for distributing said fluid antimicrobial agent within said reservoir about the periphery of said reservoir and for transporting said fluid antimicrobial agent along the length of said reservoir, said distribution means comprising a plurality of capillary grooves formed in the exterior surface of said shaft within said reservoir, said last mentioned grooves being in parallel side-by-side relationship and extending the length of said shaft within said reservoir.

5. The catheter of claim 4, wherein said shaft containing said grooves exhibits a surface contact angle with respect to said fluid antimicrobial agent which will promote distribution of said fluid antimicrobial agent along the length of said shaft and preferentially hold said fluid antimicrobial agent at the base of said grooves by capillary action.

6. A catheter for drainage of or infusion into a body cavity, said catheter comprising an elongated tubular shaft having a distal end with at least one port near said distal end to be located in said body cavity to be treated and an open proximal end adapted to be connected to a drainage or infusion conduit, a sleeve extending about and longitudinally of said shaft from a point near said at least one port toward said proximal end of said shaft, said sleeve forming a concentric reservoir for a fluid antimicrobial agent, said sleeve being permeable to the controlled passage of said fluid antimicrobial agent by diffusion, an inlet port at said proximal end of said catheter for supplying said fluid antimicrobial agent to said reservoir and for replenishing said fluid antimicrobial agent therein, said inlet port being connected by a lumen formed in the wall of said shaft and opening into said reservoir at the distal end thereof, said sleeve having a distal end sealed to said shaft, said sleeve having a proximal end sealed to said shaft, and distribution means for distributing said fluid antimicrobial agent within said reservoir about the periphery of said reservoir and for transporting said fluid antimicrobial agent along the length of said reservoir, and a one-way valved port in the wall of said tubular shaft located at the proximal end of said reservoir and permitting the flow of said fluid antimicrobial agent from said reservoir into said tubular shaft.

7. A catheter for drainage of or infusion into a body cavity, said catheter comprising an elongated tubular shaft having a distal end with at least one port near said distal end to be located in said body cavity to be treated and an open proximal end adapted to be connected to a drainage or infusion conduit, a sleeve extending about and longitudinally of said shaft from a point near said at least one port toward said proximal end of said shaft, said sleeve forming a concentric reservoir for a fluid antimicrobial agent, said sleeve being permeable to the controlled passage of said fluid antimicrobial agent by diffusion, an inlet port at said proximal end of said catheter for supplying said fluid antimicrobial agent to said reservoir and for replenishing said fluid antimicrobial agent therein, said inlet port being connected by a lumen formed in the wall of said shaft and opening into said reservoir at the distal end thereof, said sleeve having a distal end sealed to said shaft, said sleeve having a proximal end sealed to said shaft, distribution means for distributing said fluid antimicrobial agent within said reservoir about the periphery of said reservoir and for transporting said fluid antimicrobial agent along the length of said reservoir, and a one-way valved port in said sleeve located at the proximal end thereof and permitting flow of said fluid antimicrobial agent from said reservoir therethrough.

8. A catheter for drainage of or infusion into a body cavity, said catheter comprising an elongated tubular shaft having a distal end with at least one port near said distal end to be located in said body cavity to be treated and an open proximal end adapted to be connected to a drainage or infusion conduit, a sleeve extending about and longitudinally of said shaft from a point near said at least one port toward said proximal end of said shaft, said sleeve forming a concentric reservoir for a fluid antimicrobial agent, said sleeve being permeable to the controlled passage of said fluid antimicrobial agent by diffusion, an inlet port at said proximal end of said catheter for supplying said fluid antimicrobial agent to said reservoir and for replenishing said fluid antimicrobial agent therein, said inlet port being connected by a lumen formed in the wall of said shaft and opening into said reservoir at the proximal end thereof, said sleeve having a distal end sealed to said shaft, said sleeve having a proximal end sealed to one of said shaft and said filling means, and distribution means for distributing said fluid antimicrobial agent within said reservoir about the periphery of said reservoir and for transporting said fluid antimicrobial agent along the length of said reservoir, and a one-way valved port in the wall of said tubular shaft located at the distal end of said reservoir and permitting the flow of said fluid antimicrobial agent from said reservoir into said tubular shaft.

9. A urethral drainage catheter comprising an elongated tubular shaft having a distal end with at least one port near said distal end to be located in the body cavity to be drained and an open proximal end adapted to be connected to a drainage conduit, a sleeve extending about and longitudinally of said shaft from a point near said at least one port toward said proximal end of said shaft, said sleeve forming a concentric reservoir for a fluid antimicrobial agent, said sleeve being permeable to the controlled passage of said fluid antimicrobial agent by diffusion, filling means at the proximal end of said shaft for supplying said fluid antimicrobial agent to said reservoir and for replenishing said fluid antimicrobial agent therein, said sleeve having a distal end sealed to said shaft, said sleeve having a proximal end sealed to one of said shaft and said filling means, distribution means within said reservoir for distributing said fluid antimicrobial agent about and along the length of said reservoir, said distribution means comprising a plurality of capillary grooves formed in one of the inside surface of said sleeve and the exterior surface of said shaft, said grooves being in parallel side-by-side relationship and extending the length of said reservoir, an inflatable retention balloon on said shaft located between said at least one port of said shaft distal end and said distal end of said sleeve, and a fluid inlet port near said proximal end of said shaft connected to said retention balloon by a lumen formed in the wall of said shaft whereby fluid can be introduced into said retention balloon to inflate said balloon.

10. The catheter of claim 9, wherein said sleeve containing said grooves exhibits a surface contact angle with respect to said fluid antimicrobial agent which will promote distribution of said fluid antimicrobial agent along the length of said sleeve and preferentially hold said fluid antimicrobial agent at the base of said grooves by capillary action.

11. A urethral drainage catheter comprising an elongated tubular shaft having a distal end with at least one port near said distal end to be located in the body cavity to be drained and an open proximal end adapted to be connected to a drainage conduit, a sleeve extending about and longitudinally of said shaft from a point near said at least one port toward said proximal end of said shaft, said sleeve forming a concentric reservoir for a fluid antimicrobial agent, said sleeve being permeable to the controlled passage of said fluid antimicrobial agent by diffusion, an inlet port at the proximal end of said catheter for supplying said fluid antimicrobial agent to said reservoir and for replenishing said fluid antimicrobial agent therein, said inlet port being connected by a lumen formed in the wall of said shaft opening into said reservoir at the distal end thereof, and including a one-way valved outlet port at the proximal end of said reservoir formed in one of said shaft and said sleeve, said sleeve having a distal end sealed to said shaft, said sleeve having a proximal end sealed to said shaft, distribution means within said reservoir for distributing said fluid antimicrobial agent about and along the length of said reservoir, an inflatable retention balloon on said shaft located between said at least one port of said shaft distal end and said distal end of said sleeve, and a fluid inlet port near said proximal end of said shaft connected to said retention balloon by a lumen formed in the wall of said shaft whereby fluid can be introduced into said retention balloon to inflate said balloon.

12. A continuous ambulatory peritoneal dialysis catheter comprising an elongated tubular shaft having a distal end with at least one port near said distal end to be located in the body cavity to be treated and an open proximal end adapted to be connected to a conduit leading to a conventional bag of dialysis fluid, a pair of conventional proximal and distal anchoring cuffs on said catheter, said proximal anchoring cuff being surgically located just under the skin of the patient and said distal anchoring cuff being surgically located deeper in the muscle of the abdominal wall, a sleeve extending about and longitudinally of said shaft from said distal anchoring cuff beneath said proximal anchoring cuff to a position toward said proximal end of said catheter outside said patient's body, said sleeve forming a concentric reservoir for a fluid antimicrobial agent, said sleeve being permeable to the controlled passage of said fluid antimicrobial agent by diffusion, an inlet port at the proximal end of said catheter for supplying said fluid antimicrobial agent to said reservoir and for replenishing said fluid antimicrobial agent therein, said inlet port being connected by a lumen formed in the wall of said shaft and opening into said reservoir at the distal end thereof, a one-way valved outlet port at the proximal end of said reservoir formed in one of said shaft and said sleeve, and distribution means within said reservoir for distributing said fluid antimicrobial agent about and along the length of said reservoir.

13. A catheter for drainage of or infusion into a body cavity, said catheter comprising an elongated tubular shaft having a distal end with at least one port near said distal end to be located in said body cavity to be treated and an open proximal end adapted to be connected to a drainage or infusion conduit, a sleeve extending about and longitudinally of said shaft from a point near said at least one port toward said proximal end of said shaft, said sleeve forming a concentric reservoir for a fluid antimicrobial agent, said sleeve being permeable to the controlled passage of said fluid antimicrobial agent by diffusion, an inlet port at said proximal end of said catheter connected directly to said reservoir for supplying said fluid antimicrobial agent to said reservoir and for replenishing said fluid antimicrobial agent therein, said sleeve having a distal end sealed to said shaft, said sleeve having a proximal end sealed to said shaft, distribution means for distributing said fluid antimicrobial agent within said reservoir about the periphery of said reservoir and for transporting said fluid antimicrobial agent along the length of said reservoir, and a one-way valved port in the wall of said tubular shaft located at the distal end of said reservoir and permitting the flow of said fluid antimicrobial agent from said reservoir into said tubular shaft.

* * * * *

UNITED STATES PATENT AND TRADEMARK OFFICE
CERTIFICATE OF CORRECTION

PATENT NO. : 4,623,329

DATED : November 18, 1986

INVENTOR(S) : James L. Drobish, Eldon G. Spletzer and Hugh A. Thompson

It is certified that error appears in the above-identified patent and that said Letters Patent is hereby corrected as shown below:

Column 2, line 30, "urethal" should read -- urethral --.

Column 3, line 9, delete "of".

Column 8, line 8, "pasage" should read -- passage --.

Signed and Sealed this

Third Day of March, 1987

Attest:

DONALD J. QUIGG

Attesting Officer        Commissioner of Patents and Trademarks